(12) United States Patent
Jung et al.

(10) Patent No.: US 9,877,784 B2
(45) Date of Patent: Jan. 30, 2018

(54) LIGHT TRANSMITTING CABLE AND LASER SYSTEM INCLUDING THE SAME

(71) Applicant: Electronics and Telecommunications Research Institute, Daejeon (KR)

(72) Inventors: Moon Youn Jung, Daejeon (KR); Dong Hoon Song, Daejeon (KR); Won Bae Cho, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/663,085

(22) Filed: Mar. 19, 2015

(65) Prior Publication Data

US 2015/0272677 A1    Oct. 1, 2015

(30) Foreign Application Priority Data

Mar. 28, 2014  (KR) .................. 10-2014-0037003
Nov. 12, 2014  (KR) .................. 10-2014-0157417
Mar. 5, 2015   (KR) .................. 10-2015-0030742

(51) Int. Cl.
| | |
|---|---|
| *A61N 5/06* | (2006.01) |
| *A61B 18/22* | (2006.01) |
| *H04N 7/18* | (2006.01) |
| *A61N 5/10* | (2006.01) |
| *H04N 5/225* | (2006.01) |
| *A61B 90/00* | (2016.01) |

(52) U.S. Cl.
CPC ............ *A61B 18/22* (2013.01); *A61N 5/1014* (2013.01); *H04N 5/2256* (2013.01); *H04N 7/185* (2013.01); *A61B 2018/2266* (2013.01); *A61B 2090/3614* (2016.02); *A61B 2090/373* (2016.02); *A61N 2005/1022* (2013.01); *A61N 2005/1059* (2013.01); *A61N 2005/1088* (2013.01); *H04N 2005/2255* (2013.01)

(58) Field of Classification Search
CPC ............ A61B 18/22; A61B 2018/2211; A61B 2018/2266; A61B 2018/2272
See application file for complete search history.

(56) References Cited

U.S. PATENT DOCUMENTS

| | | | |
|---|---|---|---|
| 8,655,431 B2 | 2/2014 | Joos et al. | |
| 2004/0034339 A1* | 2/2004 | Stoller | A61B 18/1402 606/1 |
| 2005/0192480 A1* | 9/2005 | Toriya | A61B 1/00167 600/182 |
| 2007/0176078 A1* | 8/2007 | Takahashi | G21K 1/06 250/205 |
| 2009/0156899 A1* | 6/2009 | Konishi | A61B 1/00096 600/160 |

(Continued)

FOREIGN PATENT DOCUMENTS

KR    10-2013-0126336 A    11/2013

*Primary Examiner* — John R Downey

(57) ABSTRACT

Provided herein is a light transmitting cable for laser treatment, the cable including a first optical fiber configured to generate a high energy particle by a laser beam transmitted from a light source and to transmit the high energy particle to a target; and an image transmitting cable configured to transmit an image surrounding the target, thereby being capable of treating a tumor with relatively low power output while identifying a location of the tumor.

17 Claims, 5 Drawing Sheets

(56) References Cited

U.S. PATENT DOCUMENTS

| | | | | |
|---|---|---|---|---|
| 2010/0127183 A1* | 5/2010 | Iseki | ............... | A61N 5/1043 |
| | | | | 250/396 ML |
| 2010/0133445 A1* | 6/2010 | Noda | ............ | H05H 7/12 |
| | | | | 250/396 R |
| 2011/0038580 A1* | 2/2011 | Griffin | ............. | A61B 18/24 |
| | | | | 385/33 |
| 2011/0096385 A1* | 4/2011 | Suzuki | ............ | H05H 15/00 |
| | | | | 359/227 |
| 2011/0101244 A1* | 5/2011 | Jung | ............... | A61N 5/10 |
| | | | | 250/492.1 |
| 2012/0280138 A1* | 11/2012 | Choi | ............. | C23C 14/0005 |
| | | | | 250/423 P |

\* cited by examiner

LIGHT TRANSMITTING CABLE AND LASER SYSTEM INCLUDING THE SAME

CROSS-REFERENCE TO RELATED APPLICATION

The present application claims priority to Korean patent application numbers 10-2014-0037003 filed on Mar. 28, 2014, 10-2014-0157417 filed on Nov. 12, 2014, and 10-2015-0030742 filed on Mar. 5, 2015, the entire disclosure of which is incorporated herein in its entirety by reference.

BACKGROUND

Field of Invention

Various embodiments of the present disclosure relate to a light transmitting cable, and more particularly, to a light transmitting cable for treating a tumor, and a laser system including the same.

Description of Related Art

A conventional laser ion accelerated apparatus for treating a tumor needs a hundreds of terawatt (TW) to petawatt (PW) grade power output, and thus costs a lot, which is a disadvantage. This is because since a tumor is usually located relatively deep inside a human body, it requires high energy ions to be treated, and thus to generate the high energy ions, a high power output laser system is needed. Therefore, there is a need for a laser system structure capable of achieving a desired purpose with only low power output.

SUMMARY

Various embodiments of the present disclosure are directed to a light transmitting cable capable of being inserted inside a human body and of treating a tumor with relatively low power output while identifying a location of the tumor.

Various embodiments of the present disclosure are also directed to a laser system that includes a light transmitting cable capable of being inserted inside a human body and of treating a tumor with relatively low power output while identifying a location of the tumor.

One embodiment of the present disclosure provides a light transmitting cable for laser treatment, the cable including: at least one first optical fiber configured to generate a high energy particle by a laser beam transmitted from a light source and to transmit the high energy particle to a target; and an image transmitting cable configured to transmit an image surrounding the target.

According to the embodiment, the laser beam transmitted through the first optical fiber may be a femto-second, pico-second, or nano-second laser beam.

According to the embodiment, the first optical fiber may include a lens for focusing the transmitted laser beam.

According to the embodiment, the first optical fiber may include a thin film configured to generate the high energy particle by the transmitted laser beam, and the thin film may be located in a focal distance of the lens.

According to the embodiment, the light transmitting cable may further include a blocking plate disposed with a certain distance from the thin film of the first optical fiber in order to prevent the high energy particle generated by the first optical fiber from proceeding to any other portion besides the target.

According to the embodiment, the thin film may include a hydrogen atom or carbon atom, and may be configured to generate, by the laser beam, a proton as the high energy particle.

According to the embodiment, the image transmitting cable may be a second optical fiber cable configured to transmit visible ray reflected from the target.

According to the embodiment, at one end of the image transmitting cable, a camera for photographing the target may be mounted, and the camera may be configured to convert a photographed image into an electric signal and transmit the image through the image transmitting cable.

Another embodiment of the present disclosure provides a laser system including: a laser light source; and a light transmitting cable, wherein the light transmitting cable comprises at least one first optical fiber configured to generate a high energy particle by a laser beam transmitted from the light source and to transmit the high energy particle to a target, and an image transmitting cable configured to transmit an image surrounding the target.

According to the embodiment, the first optical fiber may include a thin film configured to generate the high energy particle by the transmitted laser beam, and the thin film may be located in a focal distance of the lens.

According to the embodiment, the image transmitting cable may consist of an endoscope configured to observe an area surrounding the target.

According to the embodiment, at one end of the image transmitting cable, a camera for photographing an image surrounding the target may be provided, and the image transmitting cable may be configured to transmit an electric signal generated from the camera.

According to the embodiment, the image transmitting cable may be an optical fiber cable configured to transmit visible ray entering from an area surrounding the target.

According to the embodiment, the laser system may further include a blocking plate provided at one end of the light transmitting cable, and configured to prevent the high energy particle generated by the first optical fiber from proceeding to any other portion besides the target.

According to the embodiment, the blocking plate may be configured such that its distance from the light transmitting cable is adjustable.

According to the light transmitting cable and laser system including the same according to the various aforementioned embodiments of the present disclosure, it is possible to treat a tumor with relatively low power output while identifying a location of the tumor.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

DETAILED DESCRIPTION

Figure 1:
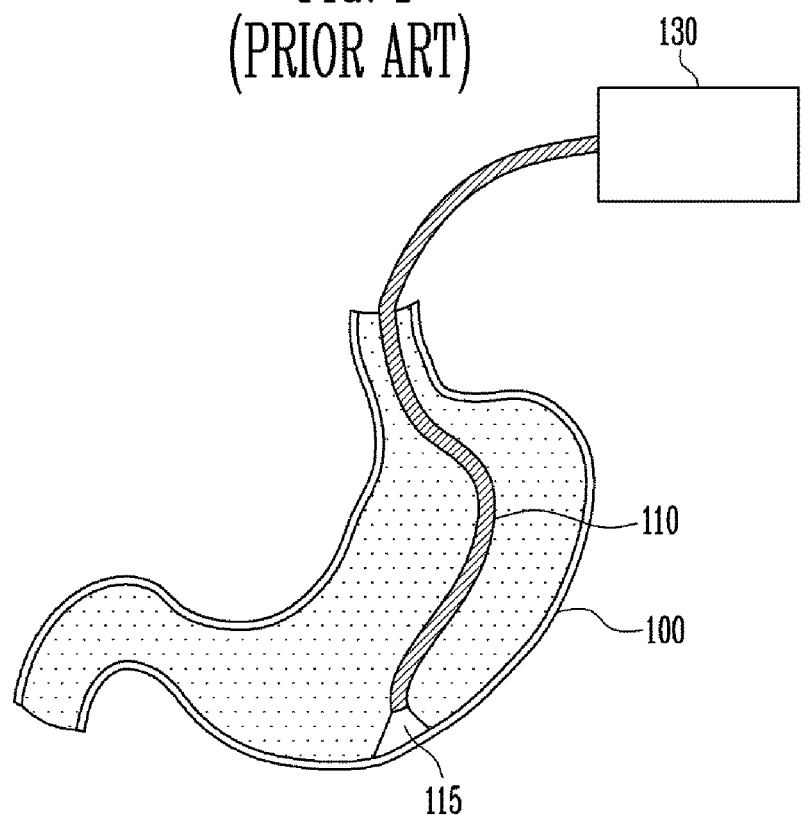
FIG. 1 is a view illustrating a structure of a conventional endoscope.

Hereinafter, embodiments will be described in greater detail with reference to the accompanying drawings. Embodiments are described herein with reference to cross-sectional illustrations that are schematic illustrations of embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but may include deviations in shapes that result, for example, from manufacturing. In the drawings, lengths and sizes of layers and regions may be exaggerated for clarity. Like reference numerals in the drawings denote like elements.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present disclosure. Furthermore, 'and/or' may include any one of or a combination of the components mentioned.

Furthermore, a singular form may include a plural from as long as it is not specifically mentioned in a sentence. Furthermore, "include/comprise" or "including/comprising" used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

It is also noted that in this specification, "connected/coupled" refers to one component not only directly coupling another component but also indirectly coupling another component through an intermediate component. On the other hand, "directly connected/directly coupled" refers to one component directly coupling another component without an intermediate component.

By focusing a pico-second~femto-second layer light to a thin film, it is possible to accelerate a proton or carbon ion. There are two types of ion accelerating models. First, the target normal sheath acceleration (TNSA) is used when the intensity of a laser is weak, that is or less than 1020 W/cm².

When a laser beam enters a thin film, electrons inside the thin film are accelerated, and thus break loose from a rear surface of the thin film to instantly exist in the form of an electron clouding. Herein, protons or cations inside the thin film remain there, and a very large electric field of or above 1012 V/cm is formed between the electron clouding on the rear surface of the thin film and the cations. By this electric field, the cations are accelerated towards the electron clouding. When their energy reaches 200 MeV, they may arrive at a tumor deep as much as 15 cm inside a human body. Herein, regardless of the incident angle of the laser beam and the thin film target, the ions are accelerated in a direction vertical to the surface of the target thin film, and that is why this model is the TNSA model. Second, there is the radiation pressure model. When the intensity of a laser is or above 1021 W/cm², ions are accelerated in the proceeding direction of the laser beam unlike in the TNSA model. The radiation pressure is a model based on the electromagnetic Lorentz force. The Lorentz force is the force applied to an object having an electric charge inside an electromagnetic field. Inside the electric field, a force of qE is applied to the object, and a force of qvxB is applied to the magnetic field. The Lorentz force is F=q(E+qxB), that is, the sum of the two forces. Herein, E represents the electric field, B represents the magnetic field, q represents the electric charge of particles, and v represents the speed of the particles. Furthermore, x represents the outer product. The accelerating principle of the ions differs depending on the intensity of the laser. Ions to which the radiation pressure model is applied have a large acceleration energy, while ions to which the TNSA model is applied have a smaller energy than in the radiation pressure model. Generally, the intensity of a laser differs depending on the size of an amplifying stage. Configuring an amplifying stage incurs cost. Thus, accelerating radiation pressure ions incurs more cost. However, accelerating ions according to the TNSA model has a problem. It is difficult to obtain energy of or above 70 MeV with the current intensity of a laser. And there are not so many types of tumors in human bodies that can be treated with the energy of 70 MeV.

Therefore, there needs to be a new configuration for treating a tumor inside a human body with low energy. Hereinafter, the configuration of the present disclosure will be explained. But before that, a conventional endoscope will be explained.

FIG. 1 is a view illustrating a structure of a conventional endoscope.

FIG. 1 illustrates an endoscope 110 for observing inside a stomach 100, a lighting 115, and an image processor 130. The lighting 115 may illuminate an inner wall of the stomach 100. The light generated from the lighting 115 may be transmitted in two methods. The first method may be used when the lighting 115 has a light source from which light is generated. In this case, the lighting may receive electric energy for generating light in the light source through a wire inside the endoscope 110. The second method is when the lighting 115 only transmits light received through a light transmitting cable, for example an optical fiber inside the endoscope 110. In this case, the light source may be included not in the lighting 115 but in the image processor 130 or in another component. Furthermore, they may be two methods of converting visible ray reflected from the inner wall of the stomach 100 into an image signal. First, a small camera may be embedded in one end (near the lighting) of the endoscope 110, and convert the light reflected from the inner wall of the stomach 100 into an electric signal, and transmit the electric signal to the image processor 130 through a wire for signal transmission inside the endoscope 110. In this case, the image processor 130 processes the electric signal. Second, the light reflected from the inner wall of the stomach 100 may be transmitted to the image processor 130 through the optical fiber inside the endoscope 110 in the format of a visible ray. In this case, the image processor 130 may convert the visible ray into an electric signal and generate an image signal.

Figure 2:
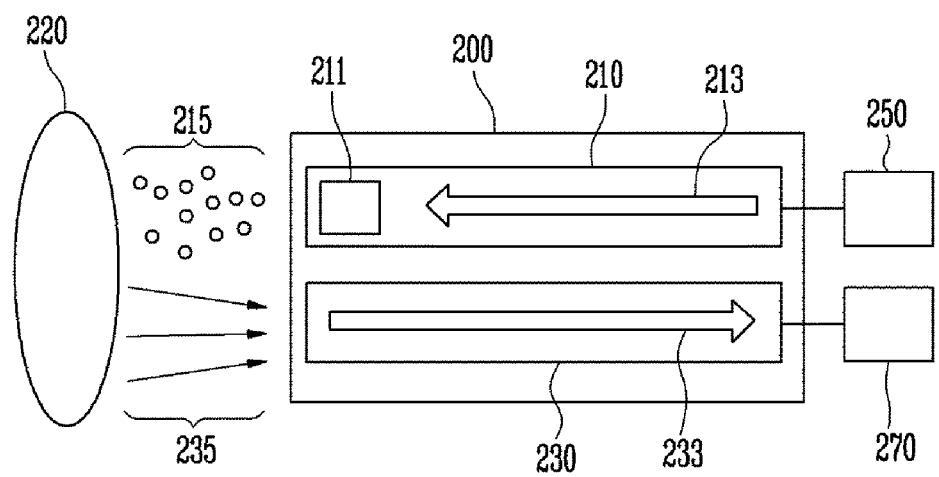
FIG. 2 is a view illustrating a laser system according to an embodiment of the present disclosure.

FIG. 2 is a view illustrating a laser system according to an embodiment of the present disclosure.

Referring to FIG. 2, the laser system according to the embodiment of the present disclosure includes a light transmitting cable 200, laser light source 250 and image processor 270. The light transmitting cable 200 includes a first optical fiber 210 and image transmitting cable 230. The light transmitting cable 200 generates a high energy particle 215 by a laser beam 213 transmitted from the light source 250 and transmits the high energy particle 215 to a target 220. The image transmitting cable 230 receives an image surrounding the target 220 in the format of visible ray 235 and transmits the image as an image signal 233 to the image processor 270. Furthermore, the light transmitting cable 200 includes a particle generator 215 for generating a high energy particle 215 by the laser beam 213. As will be explained hereinafter, the particle generator 215 may include a lens and thin film.

The light transmitting cable 200 according to the embodiment of the present disclosure may have the first optical fiber 210 and image transmitting cable 230 for generating the high energy particle 215 for treating a tumor in an integrated format packaged therein. Therefore, according to the light transmitting cable 200 according to the embodiment of the present disclosure, it is possible to generate the high energy particle while visually identifying the tumor located in an organ tissue inside the human body, thereby being capable of treating the tumor with only small energy. The light transmitting cable 200 and the configuration and operation of the laser system including the same according to the embodiment of the present disclosure will be explained in further detail hereinafter with reference to FIGS. 3a to 7.

Figure 3A:
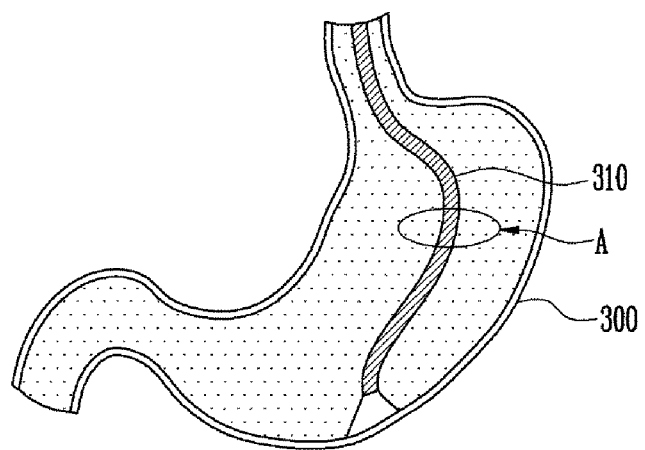
FIGS. 3a, 3b and 3c are views illustrating a light transmitting cable and its cross-section according to an embodiment of the present disclosure.
Figure 3B:
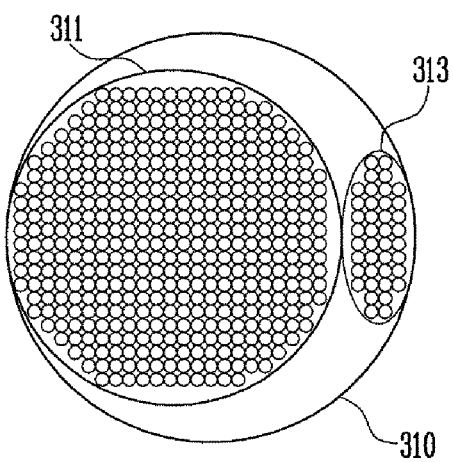
Figure 3C:
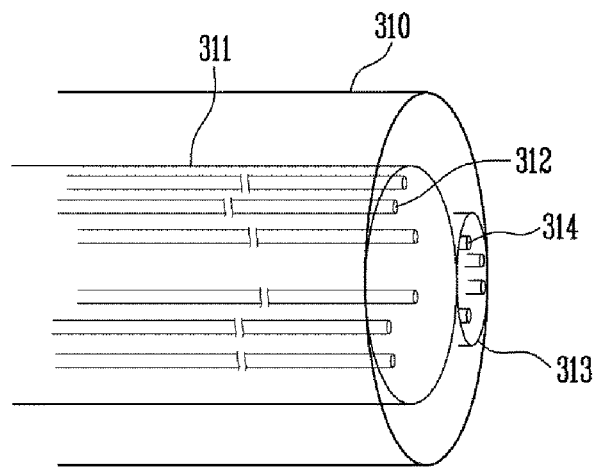

FIGS. 3a, 3b and 3c are views illustrating a light transmitting cable and its cross-section according to an embodiment of the present disclosure.

FIG. 3a illustrates a situation where a light transmitting cable 310 is inserted inside a stomach 300. Unlike in FIG. 1, the light transmitting cable 310 of FIG. 3a includes a function of a particle generator for removing a tumor besides the function of an endoscope.

FIGS. 3b and 3c are views illustrating the light transmitting cable 310 of FIG. 3a cut along cross-section A. Referring to FIGS. 3b and 3c, the light transmitting cable 310 may include a first optical fiber 311 and image transmitting cable 313. The first optical fiber 311 may consist of a bundle of a plurality of optical fibers 312. Each of the optical fiber bundles 312 may transmit a laser beam transmitted from a laser light source. The image transmitting cable 313 may consist of a single optical fiber, or of a plurality of optical fibers 314 as illustrated in FIGS. 3b and 3c. According to the light transmitting cable 310 according to the embodiment of the present disclosure, the first optical fiber 311 that is a bundle of optical fibers for transmitting a laser light source for accelerating ions and the image transmitting cable 313 for use in an endoscope may be combined in an integrated format and packaged therein. The first optical fiber 311 may consist of a bundle of a plurality of optical fibers, and may transmit a laser beam generated from a pico-second~femto-second laser light source (not illustrated) for accelerating ions. The optical transmitting cable 310 packaged as aforementioned may approach near a tumor inside the stomach 300. In this case, the light transmitting cable 310 may make the approach through the image transmitting cable 313 inside the light transmitting cable 310 for use in the endoscope. After identifying a location of the tumor, a laser beam is generated by the pico-second~femto-second laser light source (not illustrated) for accelerating ions, and the laser beam is transmitted by the first optical fiber 311, and then a proton or carbon ion is projected to the tumor from one end of the first optical fiber 311. FIGS. 3a to 3c do not illustrate the specific configuration of generating the proton or carbon ion at the one end of the first optical fiber 311. The specific configuration of generating the proton or carbon ion at the one end of the first optical fiber 311 will be explained hereinafter with reference to FIGS. 4a and 4b.

Figure 4A:
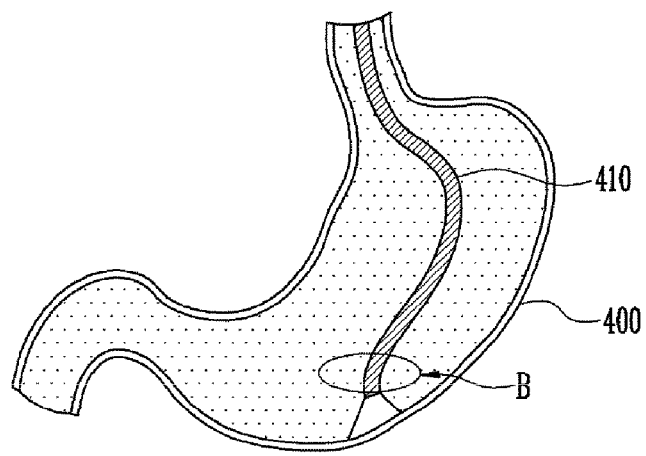
FIGS. 4a and 4b are views for explaining a thin film structure at one end of a light transmitting cable according to an embodiment of the present disclosure.
Figure 4B:
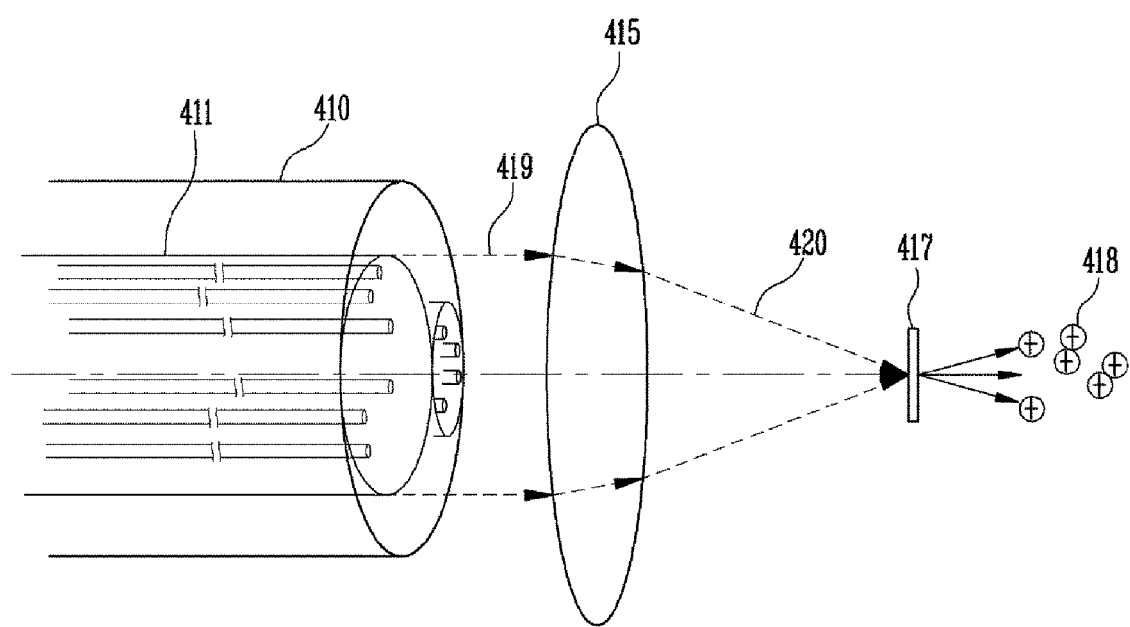

FIGS. 4a and 4b are views for explaining a structure of a thin film at one end of a light transmitting cable according to an embodiment of the present disclosure.

FIG. 4a illustrates a situation where a light transmitting cable 410 is inserted inside a stomach 400 similarly as in FIG. 3a. As aforementioned, the light transmitting cable 410 according to the embodiment of the present disclosure includes a function of a particle generator for removing a tumor besides a function of an endoscope.

FIG. 4b schematically illustrates a structure of a terminal of the light transmitting cable 410 illustrated in FIG. 4a cut along cross-section B. The terminal of the light transmitting cable 410 includes a lens 415 and thin film 417. The lens 415 may be a single lens or a lens group consisting of a plurality of lens. The lens 415 refracts a laser beam 419 transmitted by a first optical fiber 411 of the light transmitting cable 410. The thin film 417 is positioned at a focal distance position of the refracted laser beam 420. That is, the lens 415 plays a role of a focusing lens for obtaining a laser beam of a relatively high intensity at the focal distance by focusing the laser beam 419 emitted from the first optical fiber 411.

In the focal distance of the lens 415, the thin film 417 is positioned, and the laser beam 420 focused by the lens 415 enters the thin film 417. When the laser beam 420 enters the thin film 417, a baryon such as a proton or carbon ion is generated. As such, the thin film 417 plays a role of a target for generating particles.

When the thin film 417 is a target for generating a proton, a proton may be accelerated from moisture absorbed in a rear surface of the metal thin film. In another embodiment, a hydrogen atom may be contained in the thin film. In another embodiment, when accelerating a carbon ion, the carbon ion may be ionized inside a thin film made of plastic, thereby accelerating the carbon ion. Furthermore, a carbon ion or silicon atom inside a thin film made of silicon may be ionized and accelerated.

Figure 5A:
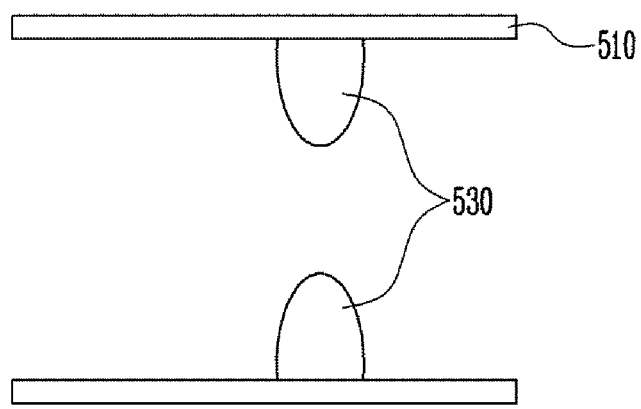
FIGS. 5a and 5b are views illustrating a tumor inside a human body.
Figure 5B:
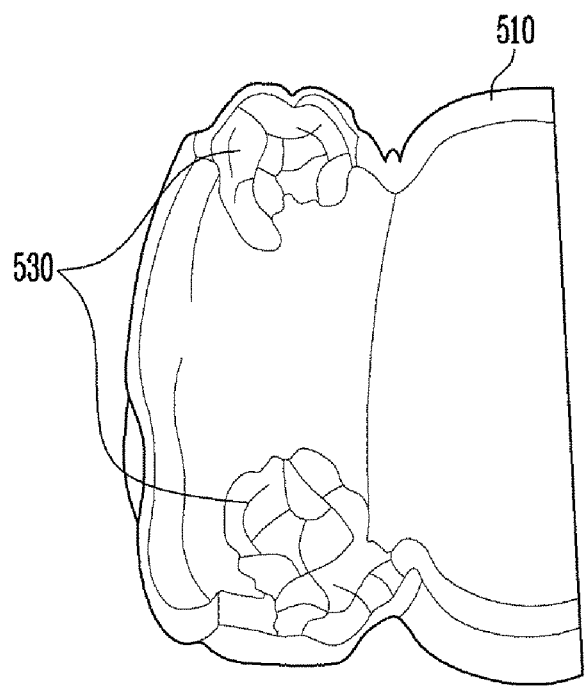

FIGS. 5a and 5b are views illustrating a tumor inside a human body. Referring to FIG. 5a, a tumor 530 is schematically illustrated in a certain organ 510 connected outside the human body such as a throat, airway, stomach, large intestine and where optical fiber bundles may be inserted. FIG. 5b illustrates the organ 510 and tumor 530 of FIG. 5a in further detail. A process of removing the tumor 530 illustrated in FIG. 5a by a laser system according to an embodiment of the present disclosure will be explained hereinafter with reference to FIG. 7.

Figure 6:
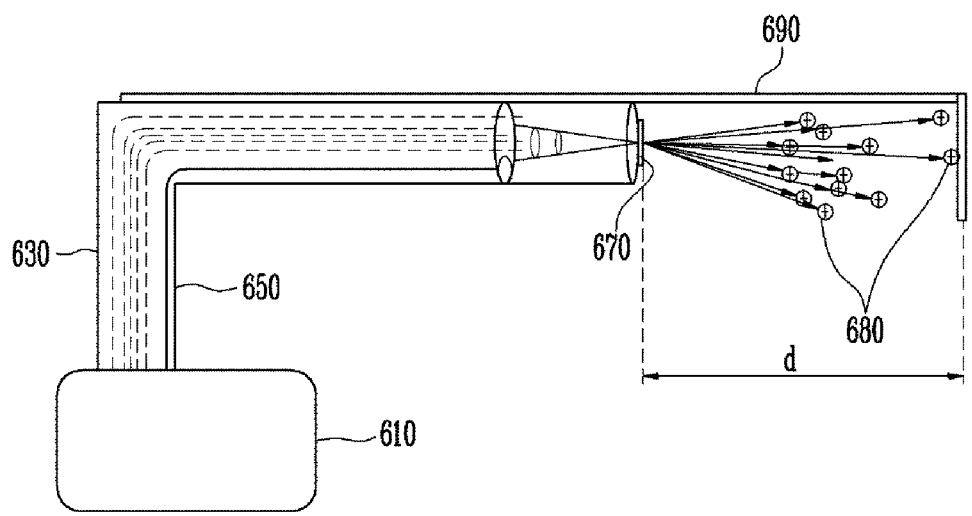
FIG. 6 is a view illustrating a laser system having a blocking plate according to an embodiment of the present disclosure.

FIG. 6 is a view illustrating a laser system having a blocking plate according to an embodiment of the present disclosure.

Referring to FIG. 6, a laser system according to an embodiment of the present disclosure includes a laser light source 610, first optical fiber 630, image transmitting cable 650 and blocking plate 690. The first optical fiber 630 may include a thin film 670 and lens. The lens is not illustrated in FIG. 6.

When a laser beam transmitted through the first optical fiber 630 is focused through the lens and enters the thin film 670 on a focal distance, an accelerated high energy particle 680 is generated from the thin film 670. As aforementioned, the high energy particle 680 may be a proton or ion. The blocking plate 690 covers as much as distance d from the thin film 670 so as to prevent the high energy particle 680 from proceeding to a human body tissue besides the tumor. Furthermore, the laser system according to the embodiment of the present disclosure is configured such that distance d between an end of the blocking plate 690 and the thin film 670 is adjustable.

Figure 7:
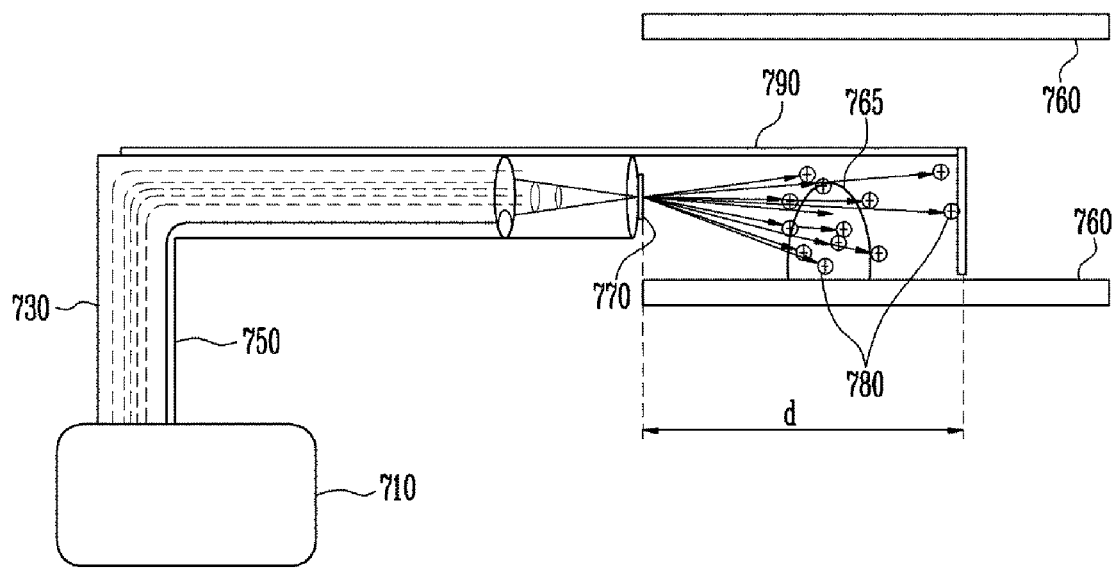
FIG. 7 is a view illustrating a situation of treating a tumor inside a human body in accordance with a laser system of FIG. 6.

FIG. 7 is a view illustrating a situation of treating a tumor inside a human body according to the laser system of FIG. 6.

Referring to FIG. 7, the laser system according to the embodiment of the present disclosure includes a laser light source 710, first optical fiber 730, image transmitting cable 750, and blocking plate 790. The first optical fiber 730 may include a thin film 770 and lens. The lens is not illustrated in FIG. 7. Furthermore, FIG. 7 illustrates an organ 760 and tumor 765 as illustrated in FIG. 5*a*.

When a laser beam transmitted from the first optical fiber 730 is focused through the lens and enters the thin film 770, an accelerated high energy particle 780 is generated from the thin film 770. As aforementioned, the high energy particle 780 may be a proton or ion. The blocking plate 790 covers as much as distance d from the thin film 770 and prevents the high energy particle 780 from proceeding to a human body tissue besides the tumor 765.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An endoscopic light transmitting cable comprising:
at least one first optical fiber configured to transmit light from a light source to generate a laser beam;
a lens configured to refract the laser beam transmitted by the first optical fiber;
a thin film positioned proximate to a focal distance of the laser beam refracted by the lens and configured to generate a high energy particle that is accelerated toward a target tissue; and
an image transmitting cable configured to transmit an image surrounding the target tissue,
wherein the image transmitting cable is disposed in a first lumen and the at least one first optical fiber is disposed in a second lumen adjacent to the first lumen.

2. The light transmitting cable according to claim 1, wherein the laser beam is received from a femto-second, pico-second, or nano-second laser source coupled to the transmitting cable, and
wherein the target tissue is a tumor.

3. The light transmitting cable according to claim 1, wherein the first optical fiber comprises a lens for focusing the transmitted laser beam.

4. The light transmitting cable according to claim 1, further comprising:
a blocking plate disposed with a certain distance from the thin film of the first optical fiber in order to block the high energy particle generated by the first optical fiber from proceeding beyond the target tissue.

5. The light transmitting cable according to claim 1, wherein the thin film comprises a hydrogen atom or carbon atom, and is configured to generate, by the laser beam, a proton as the high energy particle.

6. The light transmitting cable according to claim 1, wherein the image transmitting cable is a second optical fiber cable configured to transmit visible ray reflected from the target tissue.

7. The light transmitting cable according to claim 1, wherein at one end of the image transmitting cable, a camera for photographing the target tissue is mounted, and the camera is configured to convert a photographed image into an electric signal and transmit the image through the image transmitting cable.

8. An endoscopic laser system comprising:
a laser light source configured to generate a femto-second, pico-second, or nano-second laser beam; and
a light transmitting cable including:
a first lumen including at least one first optical fiber configured to transmit light from a light source to generate a laser beam;
a lens configured to refract the laser beam transmitted by the first optical fiber;
a thin film positioned proximate to a focal distance of the laser beam refracted by the lens and configured to generate a high energy particle that is accelerated toward a target tissue; and
a second lumen adjacent to the first lumen and including an image transmitting cable configured to transmit an image surrounding the target issue.

9. The laser system according to claim 8, wherein the image transmitting cable includes an endoscope configured to observe an area surrounding the target tissue, the target tissue being a tumor.

10. The laser system according to claim 9, wherein at one end of the image transmitting cable, a camera for photographing an image surrounding the target tissue is provided, and the image transmitting cable is configured to transmit an electric signal generated from the camera.

11. The laser system according to claim 9, wherein the image transmitting cable is an optical fiber cable configured to transmit visible ray entering from an area surrounding the target tissue.

12. The laser system according to claim 8, further comprising a blocking plate provided at one end of the light transmitting cable, and configured to block the high energy particle generated by the first optical fiber from proceeding beyond the target tissue.

13. The laser system according to claim 12, wherein the blocking plate is configured such that its distance from the light transmitting cable is adjustable.

14. The laser system according to claim 8, wherein the thin film comprises a hydrogen atom or carbon atom, or both, and is configured to generate a proton as a high energy particle.

15. The light transmitting cable according to claim 4, wherein the blocking plate is disposed at one end of the light transmitting cable, the blocking plate being movable to adjust a distance between the blocking plate and the thin film and configured to block the high energy particle generated by the first optical fiber from proceeding beyond the target tissue.

16. The light transmitting cable according to claim 1, wherein the at least one first optical fiber, the lens, and the thin film are arranged to deliver the high energy particle directly to the target tissue imaged by the image transmitting cable.

17. The light transmitting cable according to claim 8, wherein the at least one first optical fiber, the lens, and the thin film are arranged to deliver the high energy particle directly to the target tissue imaged by the image transmitting cable.

\* \* \* \* \*